(12) United States Patent
Hung

(10) Patent No.: US 8,900,860 B2
(45) Date of Patent: Dec. 2, 2014

(54) METHOD FOR EXPANDING MESENCHYMAL STEM CELLS IN LOW-DENSITY AND HYPOXIC CULTURE

(75) Inventor: Shih-Chieh Hung, Taipei (TW)

(73) Assignee: National Yang-Ming University, Taipei (TW)

( * ) Notice: Subject to any disclaimer, the term of this patent is extended or adjusted under 35 U.S.C. 154(b) by 774 days.

(21) Appl. No.: 12/627,614

(22) Filed: Nov. 30, 2009

(65) Prior Publication Data

US 2011/0129918 A1    Jun. 2, 2011

(51) Int. Cl.
| | |
|---|---|
| *C12N 5/07* | (2010.01) |
| *C12N 5/10* | (2006.01) |
| *C12N 5/071* | (2010.01) |
| *C12N 5/00* | (2006.01) |
| *C12N 5/02* | (2006.01) |
| *C12N 5/0775* | (2010.01) |

(52) U.S. Cl.
CPC .......... *C12N 5/0663* (2013.01); *C12N 2500/02* (2013.01)
USPC ........... 435/366; 435/350; 435/351; 435/352; 435/353; 435/354; 435/363; 435/325; 435/375

(58) Field of Classification Search
CPC .................................................. C12N 5/0663
See application file for complete search history.

(56) References Cited

U.S. PATENT DOCUMENTS

2007/0264712 A1    11/2007    Savant-Bhonsale

OTHER PUBLICATIONS

Hung, S-C et al, PLoS One, May 2007, 5, e416, 1-11.*
Neuhuber, B et al, Experimental Hematology, 2008, 3:1176-1185.*
Javazon, EH et al, Stem Cells, 2001, 19:219-225.*
Sotiropolous, P et al, Stem Cells, 2006, 24:462-471.*
Ren, H et al, BBRC, 2006, 347:12-21.*
Sekiya et al, Stem Cells, 2002, 20:530-541.*
Tsai, et al., "Blood", Hypoxia inhibits senescence and maintains mesenchymal stem cell properties through down-regulation of E2A-p21 by HIF-TWIST, published online Oct. 15, 2010, pp. 459-469.

* cited by examiner

*Primary Examiner* — Valerie Bertoglio
(74) *Attorney, Agent, or Firm* — Muncy, Geissler, Olds & Lowe, P.C.

(57) ABSTRACT

The present invention relates to a novel method for expanding mesenchymal stem cells (MSCs) in low-density and hypoxic condition as compared to normal air conditions traditionally used in cell culture. The present method provides rapid and efficient expansion of human MSCs without losing cellular proliferation and stem cell properties, including increase in proliferation, decrease in senescence, and increase in differentiation potential both in vitro and in vivo. The expanded MSCs by the present method may maintain normal karyotyping, and will not form tumor when transplanted into mammal.

6 Claims, 8 Drawing Sheets

METHOD FOR EXPANDING MESENCHYMAL STEM CELLS IN LOW-DENSITY AND HYPOXIC CULTURE

BACKGROUND OF THE INVENTION

Human multipotent stromal cells or mesenchymal stem cells (MSCs), capable of self renewal and differentiating into various mesenchymal tissues (Prockop, *Science* 276, 71-74, 1997), have emerged as a promising tool for clinical applications in, for example, cell-based therapy for osteogenesis imperfecta (Horwitz et al., *Nat Med* 5, 309-313, 1999) and tissue engineering in cartilage and bone (Caplan, *Tissue Eng* 11, 1198-1211, 2005). MSCs are also applied for cardiac therapeutics by preventing deleterious remodeling and improving recovery (Pittenger and Martin, *Circ Res* 95, 9-20, 2004). However, the variations in the isolation techniques, growth media, and culture conditions cause a remarkable difference in their proliferation and differentiation capacity (Pittenger, *Methods Mol Biol* 449, 27-44, 2008). Further, many studies have consistently noticed a senescent tendency of MSCs upon expansion (Bonab et al., *BMC Cell Biol* 7, 14, 2006; Shibata et al., *Stem Cells* 25, 2371-2382, 2007; and Wagner et al., *PLoS ONE* 3, e2213, 2008). Thus, the difference in stem cell properties and the senescence encountered during expansion hinder the clinical applications of MSCs.

Hypoxia has been known to regulate several cellular processes and signal transductions by the expression of Hypoxia Inducible Factor-1 (HIF-1), a heterodimer consisting of the constitutively expressed aryl hydrocarbon receptor nuclear translocator (ARNT) and the hypoxic response factor HIF-1α. HIF-1α is regulated by the cellular $O_2$ concentration and determines the transcriptional activity of HIF-1 (Semenza, *Curr Opin Genet Dev* 8, 588-594, 1998). Most of the effects of HIF-1α were investigated on cancer cells. HIF-1α, induced during ischemia, environments in the tumour nature course and after treatment, stimulates proliferation (Stoeltzing et al., *J Natl Cancer Inst* 96, 946-956, 2004), inhibits apoptosis (Akakura et al., *Cancer Res* 61, 6548-6554, 2001), induces VEGF expression and angiogenesis (Stoeltzing et al., *J Natl Cancer Inst* 96, 946-956, 2004), and promotes tumour progression and metastasis (Zhou et al., *Cancer Lett* 237, 10-21, 2006). Low-density culture improves the efficiency of expansion at the earliest passages (see, U.S. Pat. No. 7,374, 937). As described above, MSCs enriched by low-density culture method also undergo senescence and lost stem cell properties (also see Table 1). Since bone marrow, the original environment of MSCs, is hypoxic with the oxygen tension around 1 to 7% (Harrison, J. S. et al., *Blood* 99, 394, 2002), the inventors of present invention hypothesize that hypoxic culture provides more benefits than normoxic culture. Although hypoxic condition was used in the expansion of neural stem cell previously (see, US20070264712 A1), low-density culture combined with hypoxic culture has not yet been used in expanding MSCs.

Twist, a helix box transcription factor, has been known to promote tumour metastasis by inducing epithelial-mesenchymal transition (EMT) (Yang et al., *Cell* 117, 927-939, 2004). Twist cooperates with N-myc to induce tumouriogenic transformation (Valsesia-Wittmann et al., *Cancer Cell* 6, 625-630, 2004). Twist and Snail, another inducer of EMT, were proved to increase cells with cancer stem cell properties when overexpressed in breast cancer cells (Mani et al., *Cell* 133, 704-715, 2008). Further, Twist can overcome oncogene-induced senescence to complete oncogenic transformation (Ansieau et al., *Cancer Cell* 14, 79-89, 2008). Recently, the HIF-Twist axis has been proved in head and neck cancer and is involved in tumour metastasis (Yang et al., *Nat Cell Biol* 10, 295-305, 2008). Stem cells and cancer cells share a lot of similarities in gene expression, cellular processes, signal transductions, however there are few, if any, studies research the effects of HIF-Twist on stem cells.

The results of the invention provide evidences for proposing a general protocol for rapid and efficient expansion of MSCs by combining low density culture and hypoxic culture. Inventors found hypoxic culture not only prevented senescence that was noted in expanded MSCs but also increased embryonic gene expression and differentiation efficiency. The underlying mechanism mediating the increase in stemness by hypoxic culture on MSCs occurred through downregulation of E2A-p21 by the HIF-Twist pathway.

SUMMARY OF THE INVENTION

This invention is based on the unexpected discovery that human mesenchymal stem cells (MSCs) enriched by low-density culture combined with hypoxic condition well preserve the early stem cell properties. The mechanism is mediated through Twist expression by HIF-1α. Expansion under normoxia induced E2A and p21 expression, which is abrogated by overexpression of Twist, whereas siRNA against Twist upregulated E2A and p21 in hypoxic cells. The MSCs expanding by up to 100 population doublings under hypoxic conditions have a normal karyotyping, and do not form tumours when transplanted into immunodeficient mice.

In one aspect, the present invention features a method for expanding mesenchymal stem cells (MSCs) in vitro, the method comprises steps of: preparing a cell suspension containing isolated MSCs in culture medium; seeding the cell suspension at a density of 10 to 4000 MSCs/cm$^2$ under hypoxic condition with 0.05% to 15% $O_2$ in culture dish; changing the medium and subculturing the cells at a density of 10 to 4000 MSCs/cm$^2$ under hypoxic condition with 0.05% to 15% $O_2$; and recovering the MSCs after achieving semi- to full-confluence.

As used in the invention, the term "isolated mesenchymal stem cells (MSCs)" refers to MSCs isolated from human and grown in culture medium in vitro. Isolated MSCs are capable of self renewal and differentiating into various mesenchymal tissues by induction.

As used in the invention, the term "hypoxic condition" refers to a lower oxygen condition as compared to normal air conditions traditionally used in cell culture. In one embodiment, the hypoxic condition refers to a culture condition with 0.05% to 15% $O_2$.

In another aspect, this invention features a method for expanding mesenchymal stem cells (MSCs) in vitro by inducing Twist expression by HIF-1α.

Further, the present invention features an application of the mesenchymal stem cells (MSCs) expanded by the methods of present invention. The expanded MSCs preserve early stem cell properties, maintain normal karyotyping, and will not form tumor when transplanted into mammals.

Other features or advantages of the present invention will be apparent from the following drawings and detailed description of several embodiments, and also from the appending claims.

DETAILED DESCRIPTION OF THE INVENTION

Figure 1:
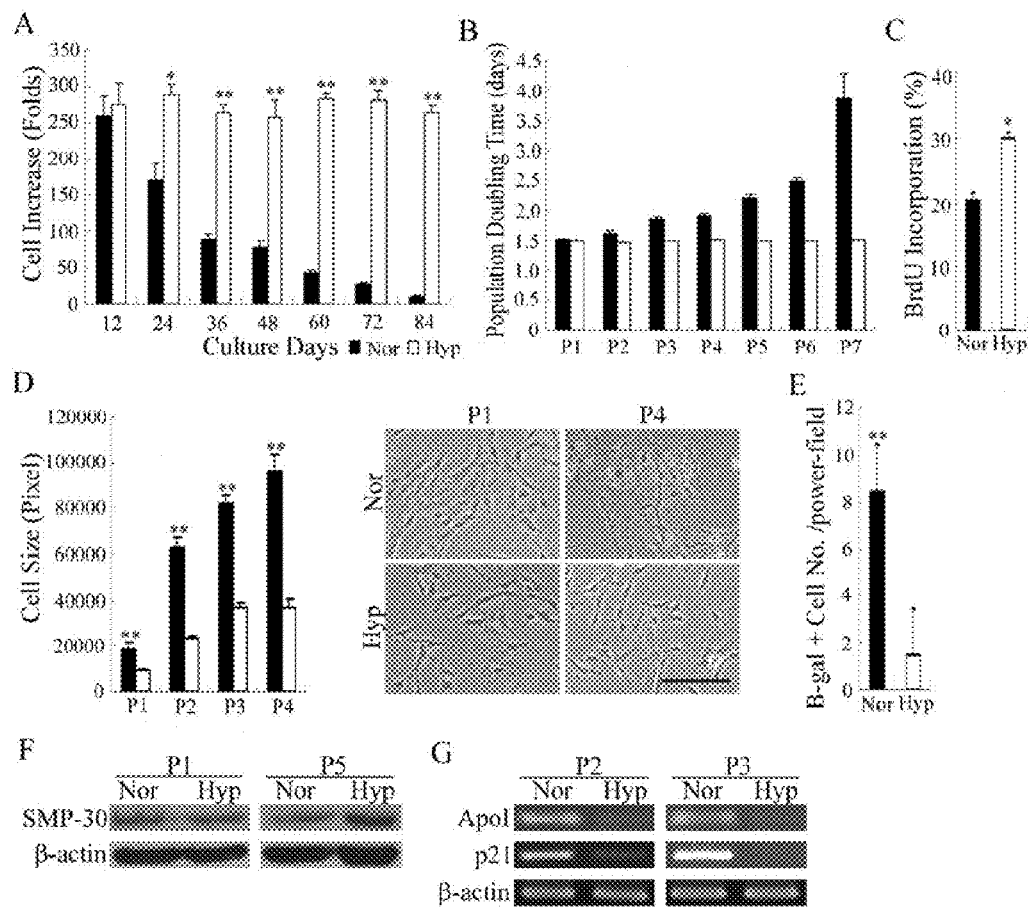
FIG. 1 shows that a Hypoxic culture increases expansion efficiency and decreases in senescence. Cells were seeded at 50 cells/cm$^2$ and cultured under normoxic and hypoxic conditions. After 12 days of cultured, the cells were recovered and reseeded at 50 cells/cm² and cultured under the same conditions. Fold of cell expansion (A) and population doubling time (B) for each passage was calculated (Pn: Passage No). C. Normoxic and hypoxic cells were incorporated with 5-bromo-2'-deoxyuridine (BrdU) for 18 hr and then detected by flow cytometry. D. Microscopic photographs of normoxic and hypoxic cells were used to analyze the cell size. E. Cells expanded under normoxic and hypoxic conditions were stained with β-galactosidase (β-gal). F. Western blotting for senescence marker protein-30 (SMP-30). G. RT-PCR analysis for markers of senescence. After expansion, the expression of senescence-related genes significantly increases under normoxic conditions compared with hypoxic conditions. [Values are mean+SD; *, $p<0.05$ and **, $p<0.01$ indicate significant variance (independent t-test) between normoxia (Nor) and hypoxia (Hyp).] Bar=50 μm. (Black blocks: normoxia; white blocks: hypoxia)

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Further, any mechanism proposed below does not in any way restrict the scope of the claimed invention.

EXAMPLE

Example 1

Hypoxic Culture Increases Expansion Efficiency and Decreases in Senescence

To rapidly expand MSCs with maintained properties, we first analyzed the expansion efficiency at a variety of seeding densities. Primary MSCs from three normal human volunteers were obtained from the Tulane Center for Distribution of Adult Stem Cells (wolfe@tulane.edu) and were prepared as described previously (Sekiya et al., Stem Cells 20, 530-541, 2002). The cells were seeded at 50 to $4\times10^3$ cells per cm² and grown in complete culture medium [CCM: α-MEM (α-minimal essential medium; Gibco-BRL, Gaithersburg, Md.), supplemented with 16.6% fetal to bovine serum (FBS), 100 units/mL penicillin, 100 μg/mL streptomycin, and 2 mM L-glutamine] in plastic culture dish with medium change twice per week.

TABLE 1

Expansion information for different seeding densities (representative data of MSCs from one dornor)

| Seeding density (cells/cm²) | Sub-culture periods (days) | Passages for 60 days | Cell number increase for each passage (folds) | Expected cell number increase for 60 days (folds) | Ratio to 4000 cells/cm² |
|---|---|---|---|---|---|
| 50 | ~12 | 5 | 252, 170, 80, 70, 48 | 11,515,392,000 | 1179.2 |
| 100 | 11~12 | 5 | 190, 121, 68, 45, 40 | 2,813,976,000 | 288.2 |
| 1000 | ~10 | 6 | 18, 18, 16, 15, 14, 11 | 11,975,040 | 1.2 |
| 4000 | 5~7 | 10 | 5 for each passage | 9,765,625 | 1.0 |

As showed in Table 1, the increase in seeding density caused a decrease in expansion efficiency. Cells seeded at low density around 50 cells/cm², increased cell numbers by up to 170-250 fold for the earliest passages. Cells seeded at high density around 1000 to 4000 cells/cm² increased cell number 5 fold for each week. However, we observed a decrease in expansion efficiency if cells were continuously expanded at low density. Accumulatively, low density culture increased cell numbers more than $10^{10}$ fold within 60 days, according to a 1000 fold of the increase in high density culture.

We then examined if hypoxic culture (1% $O_2$) could prevent low density culture-induced decrease in expansion efficiency. For hypoxic culture, cells were cultured in a gas mixture composed of 94% $N_2$, 5% $CO_2$, and 1% $O_2$. For maintenance of the hypoxic gas mixture, we used an incubator with two air sensors, one for $CO_2$ and the other for $O_2$; the $O_2$ concentration was achieved and maintained using delivery of nitrogen gas ($N_2$) generated from a liquid nitrogen tank or a tank contains pure $N_2$. If $O_2$ percentage rose above the desired level, $N_2$ gas was automatically injected into the system to displace the excess $O_2$.

The expansion rate was the same for both normoxic (21% $O_2$) and hypoxic culture at the earliest passages, but was significantly less under normoxic conditions than hypoxic conditions after passage 2 (FIG. 1A). The population doubling time (PDT) increased for the increase in passage number under normoxic conditions, however, the PDT remained the same as the earliest passages under hypoxic conditions (FIG. 1B). For a clear insight into the factors causing the dramatic difference under normoxic and hypoxic conditions, the proliferation capacity and the expression of senescence markers were evaluated. The BrdU incorporation rate was significantly higher in hypoxic cells compared to normoxic cells (FIG. 1C). Increased cell growth was noted in $O_2$ between 1% to 7%. Further, the decrease in cellular proliferation of normoxic cells was also associated with an increase in cell size with a broad morphology (FIG. 1D), a representative picture for cellular senescence in MSCs (Sekiya et al., *Stem Cells* 20, 530-541, 2002). In addition, senescence as assayed by the expression of senescence-associated β-galactosidase revealed a significant increase in normoxic cells (FIG. 1E). Western blotting also revealed a decrease in Senescence marker protein-30 (SMP-30) in late-passage MSCs under normoxic conditions, which was down-regulated with senescence and aging (Fujita et al., *Mech Ageing Dev* 107, 271-280, 1999) (FIG. 1F). RT-PCR showed an increase of ApoI and p21, markers of senescence, in normoxic cells compared to hypoxic cells (FIG. 1G). Cells under normoxic conditions began to cease proliferation and were difficult to subculture after passage 6 to 7, whereas, cells under hypoxic conditions can further be expanded without significant loss of proliferation capacity. Similar results were also demonstrated with MSCs derived from another two donors. Taken together, these data suggest low density culture expanded MSC with a decrease in proliferation capacity and an increase in senescence; however, combining low density and hypoxic culture expanded MSCs without losing proliferation capacity and inducing senescence.

Example 2

Hypoxic Culture Increases Stemness of Mesenchymal Stem Cells

In this example, the expansion insults on the stem cell properties of MSCs under normoxic and hypoxic conditions were examined. Cells under both conditions had the same profiles of surface CD markers; they are consistently positive for CD44, CD73, CD90, 105 and CD166, putative markers of MSCs, but negative for CD34 and CD133, the markers of haematopoietic stem cells, and CD45, the marker of haematopoietic cells (FIG. 2A).

Stemness of MSCs could be assayed by the potential to differentiate along osteogenic, adipogenic and chondrogenic lineages. For in vitro differentiation into osteoblasts, adipocytes and chondrocytes, cells were induced in osteogenic induction medium [OIM: DMEM-LG supplemented with 10% FBS, 50 µg/mL ascorbate-2 phosphate), $10^{-8}$ M dexamethasone and 10 mM β-glycerophosphate], adipogenic induction medium [AIM: DMEM-LG supplemented with 10% FBS, 50 µg/mL ascorbate-2 phosphate, $10^{-7}$ M dexamethasone, 50 µM indomethacin, 0.45 mM 3-isobutyl-1-methylxanthine and 10 µg/mL insulin], and chondrogenic induction medium [CIM: cell pellets in serum-free DMEM-LG supplemented with ITS+ (GIBCO) and 10 ng/mL TGF-β1 (Preprotech, Rocky Hill, N.J.)], respectively. After the appearance of morphologic features of differentiation, cells treated in OIM and AIM were stained for Alizarin Red S (ARS) and Oil-red O, respectively. Cells induced in CIM were prepared for Alcian Blue staining and immunohistochemistry. For immunohistochemistry, paraffin sections were initially incubated with blocking serum, probed with a monoclonal antibody against human type II collagen (Chemicon; Temecula, Calif.), then reacted with an alkaline phosphatase (AP)-conjugated goat anti-mouse IgG antibody, and finally processed for AP-Vector Red staining (Vector; Burlingame, Calif.). For in vivo osteogenic differentiation, $10^6$ cells delivered in ceramic cube were induced in OIM. After 1 week of induction, the cell-contained constructs were transplanted s.c. to the immunodeficient mice by surgical procedures. The specimens were analyzed by Mallory Trichrome staining 4 weeks later.

Figure 2:
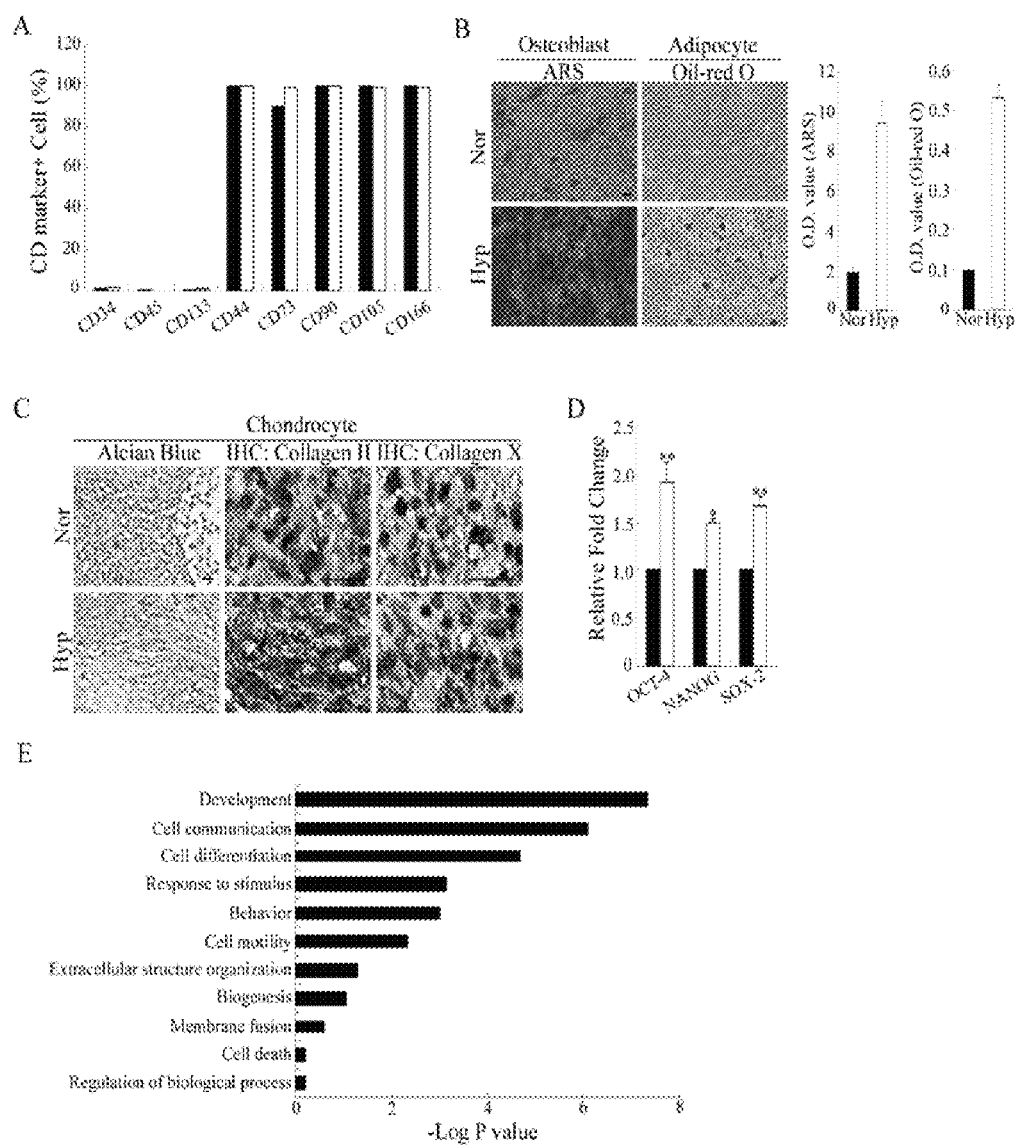
FIG. 2 shows that Hypoxic culture increases in stemness. Cells were seeded at 50 cells/cm² and expanded under normoxic and hypoxic conditions. A. Flow cytometry for detecting surface CD markers. B & C. Hypoxic cells increase in differentiation potential into osteoblasts, adipocytes and chondrocytes. B. Normoxic and hypoxic cells were induced to differentiate to osteoblasts and adipocytes, and stained by ARS and Oil-red 0, respectively. Stained dye was extracted and OD values were measured. C. Normoxic and hypoxic cells were induced to differentiate to chondrocytes, and Alcian Blue staining and immunohistochemical study for collagen II and X were performed. D. Quantitative RT-PCR for expression of embryonic transcription factors. E. Global gene expression profiles of normoxic and hypoxic cells were analyzed by microarray and GO classification for genes increased in hypoxic cells were performed. [Values are mean+SD; *, $p<0.05$ and **, $p<0.01$ indicate significant variance (independent t-test) between Nor and Hyp.] Bar=20 μm. (Black blocks: normoxia; white blocks: hypoxia)
Figure 3:
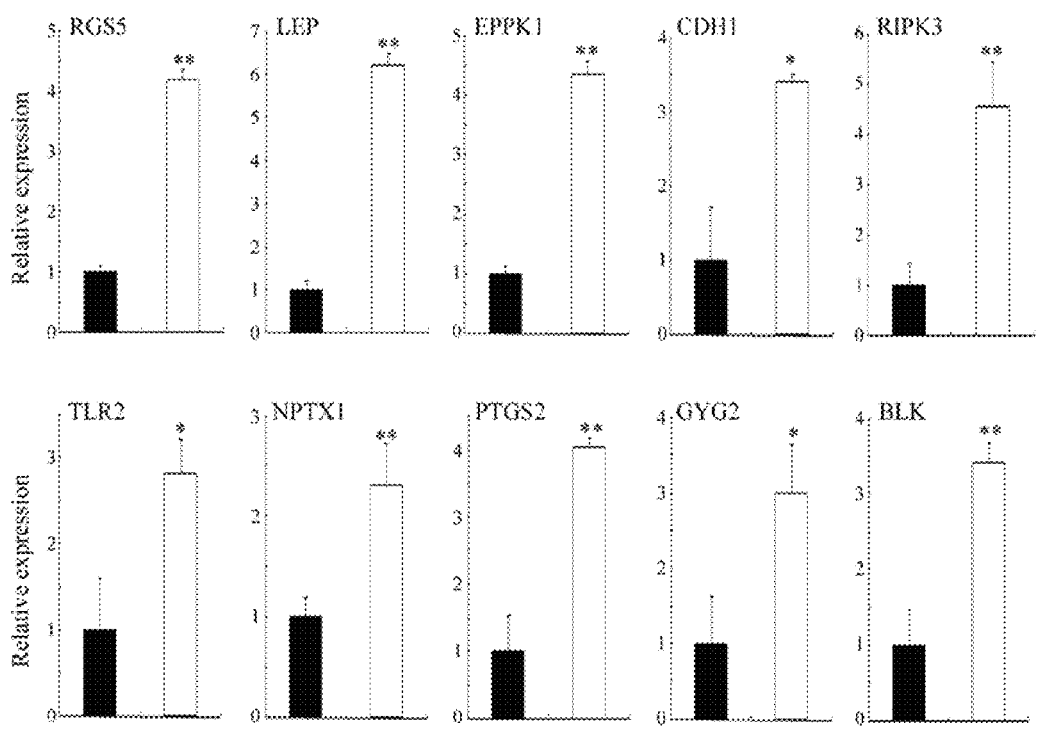
FIG. 3 shows diagrams of Quantitative RT-PCR confirming the reliability of microarray analysis. Cells were seeded at 50 cells/cm2 and cultured under normoxic and hypoxic conditions, and mRNA was used for quantitative RT-PCR analysis of genes increased in hypoxic cells. [Values are mean+SD; *, $p<0.05$ and **, $p<0.01$ indicate significant variance (independent t-test) between Nor and Hyp.] (Black blocks: normoxia; white blocks: hypoxia)

Interestingly, MSCs expanded at the low density under normoxic conditions lost the potential for all the differentiation even at passage 2 or 3, especially for adipogenic and chondrogenic differentiation, while cells under hypoxic conditions preserved the same potential for versatile differentiation as the earliest passage cells (FIGS. 2B & 2C). To understand whether the decrease in MSC efficiency under normoxic culture was associated with a change in gene expression profile, we examined the expression of embryonic transcriptional factors. Hypoxic cells had higher mRNA levels of embryonic transcription factors, such as OCT-4, NANOG and SOX-2 compared with normoxic cells (FIG. 2D). Because the gene expression profiles of developmental and differentiation-associated genes were also used to compare pluripotency or stemness in stem cells (Ramalho-Santos et al., *Science* 298: 597-600, 2002), we further used microarray to compare the gene expression profiles between both cells. Interestingly, hypoxic cells increased gene expression in genes with GO classification in development and cell differentiation (FIG. 2E). We performed real-time PCR for a set of ten genes that were detected as differentially expressed under hypoxic and normoxic conditions to confirm the reliability of the microarray results. All ten genes (RGS5, LEP, EPPK1, CDH1, RIPK3, and TLR2, NPTX1, PTGS2, GYG2, BLK) showed similar expression ratios between PCR data and microarray data generated using total RNA of MSCs from three individual donors (FIG. 3). These data taken together suggest MSCs cultured at low density lost the differentiation potential and the expression of genes associated with pluripotency, and hypoxic culture increased stemness compared with normoxic culture.

Example 3

Hypoxic Culture or HIF-Twist Bypasses Senescence and Increases Stemness by Suppressing p21 Expression To clarify the anti-senescence effects of hypoxic culture, we compared MSC proliferation and apoptosis between normoxic and hypoxic cultures by analyzing the cell cycle phase distribution. FACS analysis of hypoxic cells revealed a marked reduction in cells in the G0/G1 phase and a compensatory increase in cells in S and G2/M phases compared with normoxic cells (FIG. 4A), suggesting hypoxic culture increased cell proliferation by modulating cell cycle entry. In addition, there was only a very small population of cells in the sub-G1 phase of both the hypoxic and normoxic cells (data not shown), suggesting cell apoptosis is not the main aspect hypoxic culture mediates to resist replicative senescence.

Because cell cycle regulatory proteins and their inhibitors are involved in to cellular senescence of human fibroblasts (McConnell et al., *Curr Biol* 8, 351-354, 1998; Stein et al., *Mol Cell Biol* 19, 2109-2117, 1999), we therefore examined their involvement in the replicative senescence of MSCs by Western blotting. Cell extracts were prepared with M-PER (Pierce, Rockford, Ill.) plus protease inhibitor cocktail (Halt™; Pierce) and protein concentrations were determined using the BCA assay (Pierce). Aliquots of protein lysates were separated on SDS-10% polyacrylamide gels and transferred to PVDF membrane filters, which were blocked with 5% blotting grade milk (Bio-Rad, Hercules, Calif.) in TBST (20 mM Tris-HCl [pH 7.6], 137 mM NaCl, 1% Tween 20). Membranes were then probed with the indicated primary antibodies, reacted with corresponding secondary antibodies, and detected using a chemiluminescence assay (Millipore). Membranes were exposed to X-ray film to visualize the bands (Amersham Pharmacia Biotech, Piscataway, N.J.). The primary antibodies included anti-Twist, anti-NANOG, anti-OCT3/4, anti-SOX-2, anti-HIF-1-α, anti-E2A, anti-p21, anti-CDK2, anti-CDK4, anti-cyclin D1, anti-MDM2, anti-p27 and anti-β-actin (Santa Cruz). The secondary antibodies included Horseradish peroxidase-conjugated donkey anti-rabbit or sheep anti-mouse antibodies (Santa Cruz).

Figure 4:
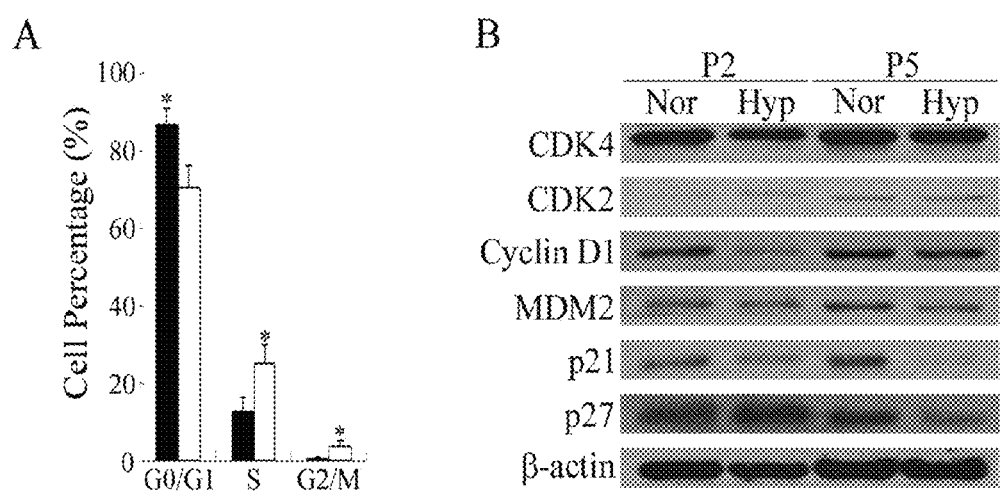
FIG. 4 shows that Hypoxic culture increases cells in the S phase and suppresses p21 expression. A. Cell cycle distribution was analyzed in normoxic and hypoxic cells by propidium iodide (PI) staining followed by flow cytometric analysis. B. Western blotting for cell cycle-related proteins. [Values are mean+SD; *, $p<0.05$ and **, $p<0.01$ indicate significant variance (independent t-test) between Nor and Hyp.] (Black blocks: normoxia; white blocks: hypoxia)

The expression level of p53 was not detectable under both hypoxic and normoxic conditions (data not shown). There was no obvious difference between CDK4 and CDK2 between hypoxic and normoxic culture both at passage 2 and 5 (FIG. 4B). In addition, the expression levels of cyclin D1 and MDM2 were slightly decreased in hypoxic culture compared with normoxic culture. Interestingly, the p21 protein level was induced at the late passage compared with the early passage of normoxic culture, while its expression was slightly downregulated at the late passage of hypoxic culture (FIG. 4B). However, the p27 level was not different between early and late passage of normoxic culture, although the p27 level was slightly downregulated at the late passage under hypoxic culture (FIG. 4B). Senescent cells increased in the p21 level and the bypass of senescence can be induced by disrupting the p21 gene in normal human fibroblasts (Afshari et al., *Cell Growth Differ* 7, 979-988, 1996; Brown et al., *Science* 277, 831-834, 1997). Thus, these data suggest replicative senescence in MSCs under normoxic conditions and the bypass of replicative senescence in hypoxic culture may be mediated by regulating the p21 protein.

Figure 5:
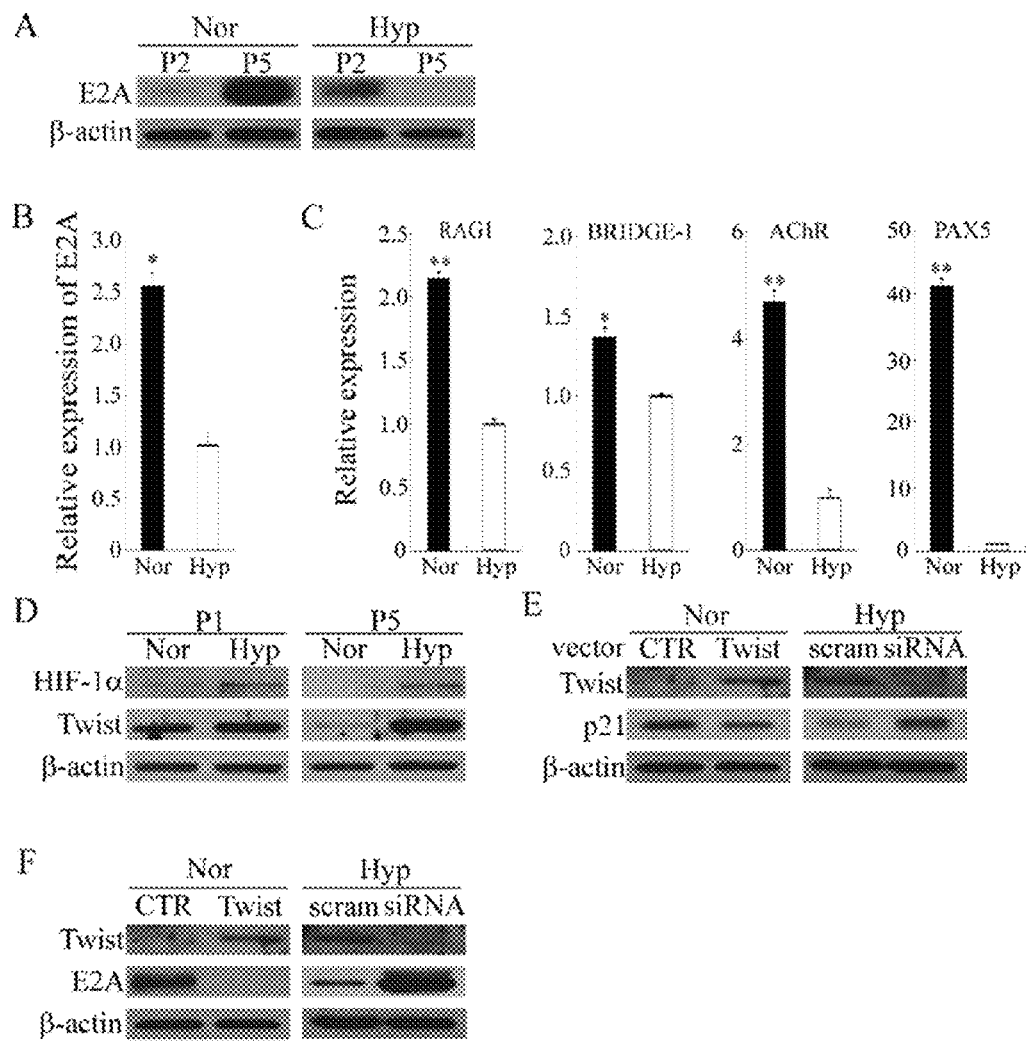
FIG. 5 shows diagrams of Western blotting (A) and quantitative RT-PCR (B) for E2A expression illustrating that HIF-Twist inhibits p21 expression via suppressing E2A protein level and activity. C. E2A downstream target gene expression was detected by quantitative RT-PCR. D. Western blotting for HIF-1α and Twist. E & F. Cell lysates were detected by Western blotting. E. As compared with control vectors, overxpression of Twist in normoxic cells inhibits the expression of p21 and siRNA against Twist in hypoxic cells induces p21 expression. F. As compared with control vectors, overexpression of Twist in normoxic cells inhibits the expression of E2A and siRNA against Twist in hypoxic cells induces E2A expression. (Black blocks: normoxia; white blocks: hypoxia)

The helix-loop-helix transcription factor E2A plays important roles in suppressing cell growth by transcriptionally activating the p21 gene (Prabhu et al., *Mol Cell Biol* 17, 5888-5896, 1997). Interestingly, expansion under normoxic conditions was associated with a marked increase in E2A protein level, whereas E2A level was slightly downregulated under hypoxic conditions (FIG. 5A). Similarly, the E2A mRNA level (FIG. 5B) and expression of downstream target genes of E2A were increased in normoxic cells compared with hypoxic cells (FIG. 5C). These data suggest senescence-induced by p21 expression in normoxic cells may be mediated by upregulating E2A expression and activity.

Figure 6:
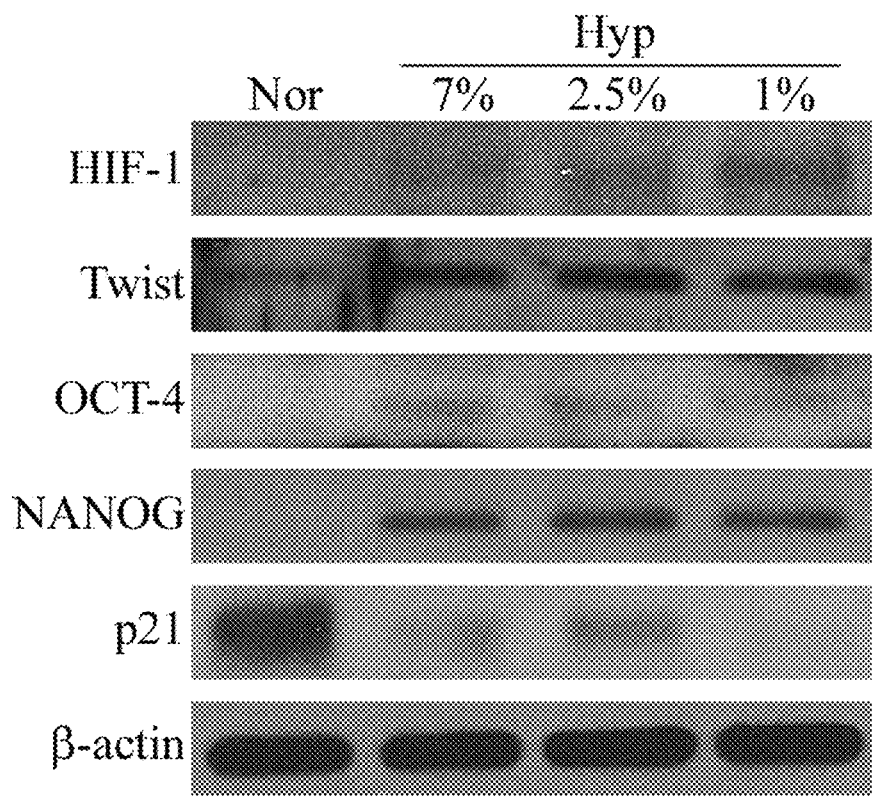
FIG. 6 shows a diagram of Western blotting illustrating that hypoxic culture at different oxygen concentration increases expression of HIF, Twist and embryonic factors. Cells at passage 7 were seeded at 50 cells/cm² and cultured under normoxic (21% $O_2$) and hypoxic conditions with oxygen concentration from 1% to 7% for 12 days.

To clarify the upstream signaling of E2A, we analyzed the expression of Twist, which is upregulated by HIF-1α (Yang et al., *Nat Cell Biol* 10, 295-305, 2008), and generates cells with stem cell properties by EMT (Mani et al., Cell 133, 704-715, 2008). Interestingly, normoxic cells expressed a very low level of HIF-1α and a base level of Twist, and downregulation of Twist was noted after expansion, while HIF-1 and Twist genes were increased under hypoxia than normoxia and expansion under hypoxia did not induce a loss of Twist expression (FIG. 5D). An increase in HIF-1 and Twist expression was observed at $O_2$ between 1% to 7% (FIG. 6). Further, hypoxic culture with $O_2$ between 1% to 7% also increased the expression of embryonic factors (FIG. 6). The expression of HIF-2α, however, was the same between normoxic and hypoxic cells (data not shown).

E2A-dependent upregulation of p21 is inhibited by Twist in osteoblast-like cells (Funato et al., *Mol Cell Biol* 21, 7416-7428, 2001). Expectedly, ectopic expression of Twist under normoxia inhibited the expression of p21 (FIG. 5E). However, we also noted siRNA against Twist under hypoxia, a condition with less expression of E2A, induced p21 expression (FIG. 5E), suggesting Twist-induced suppression of p21 was not only mediated by inhibiting the p21 inducing activity of E2A. To clarify the extra mechanism that Twist mediated to inhibit p21 expression, we examined if Twist directly regulated E2A expression. Ectopic expression of Twist under normoxia inhibited the expression of E2A (FIG. 5F), and siRNA against Twist under hypoxia induced E2A expression (FIG. 5F). These data all together suggest HIF-Twist inhibited p21 expression by suppressing both the E2A protein level and activity.

Figure 7:
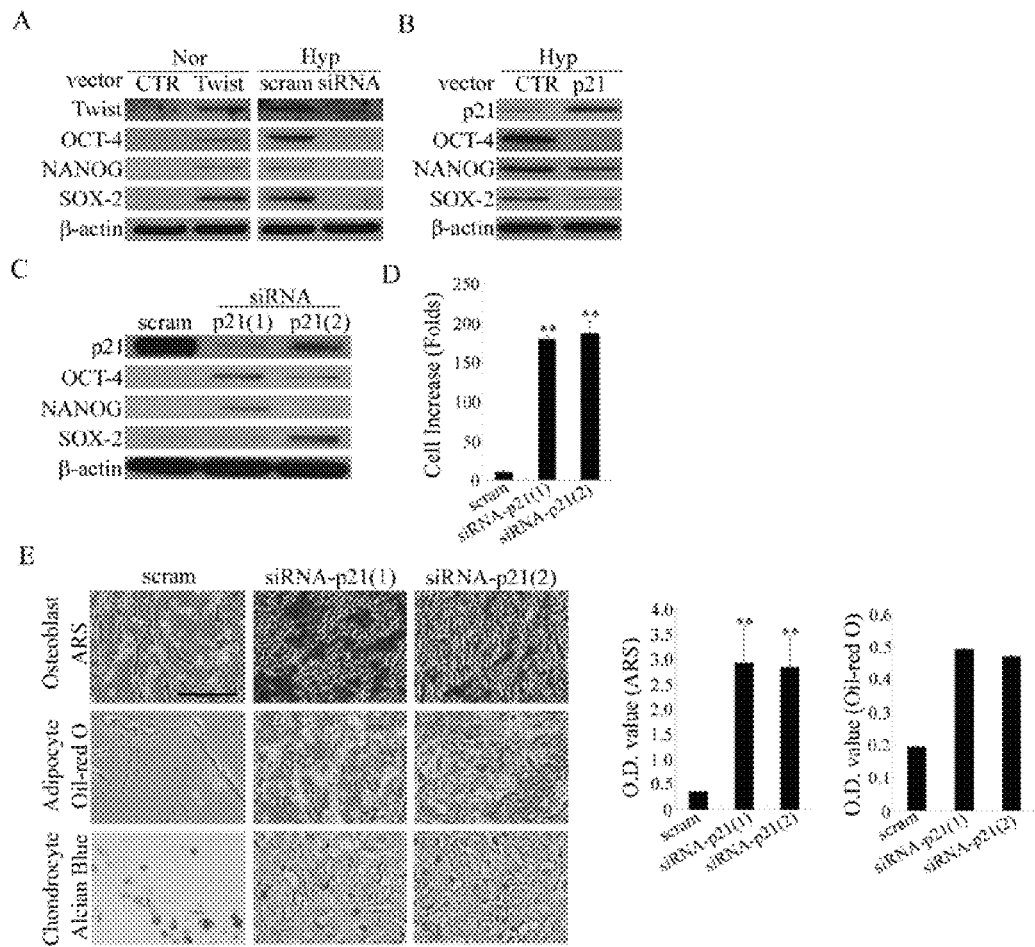
FIG. 7 shows that hypoxia or HIF-Twist increases stemness via suppressing p21. A, B, & C are Western blotting for embryonic transcription factors after cells modified with Twist expression. D. Normoxic cells were cultured 12 days after p21 knockdown in low density culture and cell numbers were counted. E. Normoxic cells after stable transfection of siRNA against p21 were differentiated into osteoblasts, adipocytes and chondrocytes, and achievements of differentiation were analyzed by staining with ARS, Oil-red O and Alcian Blue, respectively. O.D. values of ARS and Oil-red O were analyzed for quantifying osteoblast and adipocyte differentiation, respectively. Knockdown of p21 increases the differentiation potential to osteoblasts, adipocytes and chondrocytes. Bar=50 μm.

To clarify the role of Twist in Hypoxia-induced enhancement of stemness in MSCs, we analyzed the level of pluripotency transcription factors in cells modified with Twist expression. Ectopic expression of Twist under normoxia increased the expression of OCT-4, NANOG and SOX-2, whereas siRNA against Twist inhibited the expression of OCT-4, NANOG and SOX-2 in hypoxic cells (FIG. 7A). Because HIF-Twist inhibits E2A-induced p21 expression, we therefore examined whether hypoxia enhanced expression of these factors by suppressing p21. Interestingly, overexpression of p21 in hypoxic cells induced a decrease in the expression of OCT-4, NANOG and SOX-2 (FIG. 7B), while siRNA against p21 in normoxic cells upregulated OCT-4, NANOG and SOX-2 compared to scrambled siRNA (FIG. 7C). Further, siRNA against p21 in normoxic cells not only stimulated cell growth (FIG. 7D), but also increased differentiation potential to osteoblasts, adipocytes and chondrocytes (FIG. 7E). Conversely, overexpression of p21 induced a decrease in proliferation capacity, loss of differentiation capacity, and premature cell growth arrest in hypoxic cells (data not shown). These data suggest that hypoxia or HIF-Twist increases stemness in MSCs by suppressing p21, and further prove the concept that the lifespan, efficiency, and stemness of MSCs can be controlled by modifying the culture conditions or the corresponding signaling pathways. Therefore, hypoxic culture or activation of HIF-Twist pathway may provide a great amount of MSCs with good efficiency for clinical applications.

Example 4

Hypoxic Cells have a Normal Karyotype and an Untransformed Phenotype

To prove the safety by expanding MSCs under hypoxic conditions, MSCs from three individual donors that were expanded more than 70-100 population doublings were analyzed for karyotyping and transplanted into NOD-SCID mice. All of the three MSCs still proliferated well and could be expanded with low density culture. Karyotyping demonstrated normal chromosome (FIG. 8A) and no tumour developed at 3 months after transplantation (data not shown). These data demonstrate the safety to expand MSCs under low density and hypoxic conditions.

Since MSCs have been used for clinical therapy of skeleton diseases such as osteoarthritis, we investigated the potential of transplanted MSCs to differentiate into bone, fat and cartilage in vivo. For in vivo chondrocyte differentiation, cells were encapsulated with alginate as described before (Ma et al., *J Biomed Mater Res A* 74, 439-446, 2005) and then induced in CIM for 1 week. After 1 week of induction, the alginate-encapsulated cells were transplanted s.c. to the immunodeficient mice by surgical procedures. The specimens were analyzed by Alcian blue and Type 11 collagen immunohistochemistry staining 4 weeks later. For in vivo adipocyte differentiation, 1 µg/mL bFGF in 100 µL, matrigel (BD Biosciences, San Jose, Calif.,) was mixed with or without (serves as control) $1 \times 10^6$ cells, and was injected immediately to the subcutaneous layer of immunodeficient mice. The specimens were analyzed by Sudan IV staining in frozen sections 3 weeks later.

Figure 8:
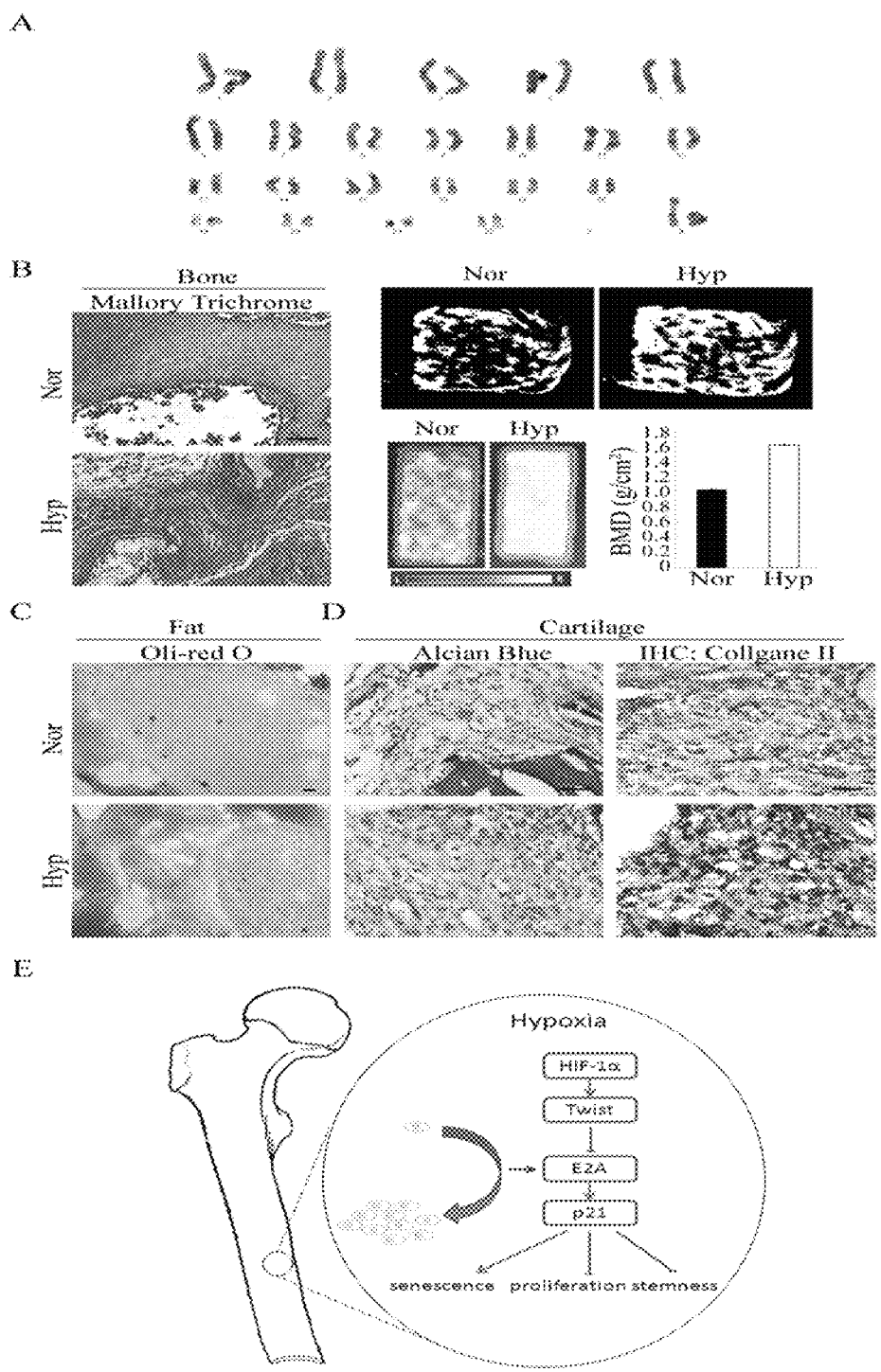
FIG. 8 shows the summaried results for elaborating the safety and efficiency of hypoxic culture. A. Karyotyping analysis shows hypoxic MSCs have normal karyotype. B. Mallory Trichrome staining shows hypoxic cells increase in collagen synthesis (Left). Micro-CT scanning shows hypoxic cells increase in bone formation (Right upper). DEXA study shows hypoxic cells increase in bone mineral density (BMD) (Right lower). C. The Oil-red O staining shows hypoxic cells increase in the accumulation of fat droplets. D. Alcian Blue staining and immunohistochemistry for type II collagen demonstrate hypoxic cells increase in the synthesis of proteoglycan and type II collagen. E. Summary of signaling pathways involving HIF-Twist and E2A-p21 in controlling senescence, proliferation and stemness of mesenchymal stem cells under hypoxic conditions. Bar=50 μm.

Compared with normoxic MSCs, hypoxic MSCs delivered in ceramic cube and induced in osteogenic medium increased in Mallory Trichrome staining after transplantation into immunodeficient mice (FIG. 8B). Further, micro-CT scans and DEXA analysis demonstrated the ceramic cubes delivered with hypoxic cells increased in bone formation and had a greater BMD as compared with normoxic cells (FIG. 8B). Hypoxic cells also increased in Oil-red O staining while mixed with basic FGF and transplanted in immunodeficient mice (FIG. 8C). Hypoxic cells when encapsulated in alginate beads and induced in chondrogenic medium increased in Alcian Blue staining and immunohistochemistry for type II collagen after transplantation into immunodeficient mice (FIG. 8D). These data demonstrate the superior efficiency of hypoxic MSCs for skeleton tissue regeneration.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for expanding mammalian mesenchymal stem cells (MSCs) in vitro, which comprises:
   a. preparing a mammalian cell suspension containing MSCs in culture medium;
   b. seeding the mammalian cell suspension at a density of 50 to 1000 cells/cm² under hypoxic condition with 1 to 7% $O_2$ in culture dish;
   c. changing the medium and subculturing the cells at a density of 10 to 1000 cells/cm² under hypoxic condition with 1 to 7% $O_2$ for at least 2 passages; and
   d. recovering the MSCs after achieving semi- to full-confluence.

2. The method of claim 1, wherein the MSC is isolated from human.

3. The method of claim 1, wherein the culture dish is plastic culture dish.

4. The method of claim 1, wherein the culture dish without any coating.

5. A population of mammalian mesenchymal stem cells (MSCs) expanded by the method of claim 1, which preserves early stem cell properties, maintains normal karyotyping, and will not form tumors when transplanted into mammals.

6. The population of mammalian MSCs of claim 5, which maintains normal karyotyping after population doubling for 100 times.

* * * * *